United States Patent [19]

Shanmuganathan

[11] Patent Number: 5,525,132
[45] Date of Patent: Jun. 11, 1996

[54] YEASTS AS A BIOCONTROL FOR MICROBIAL DISEASES OF FRUIT

[75] Inventor: Navaragnam Shanmuganathan, Doncaster, Australia

[73] Assignee: Daratech Proprietary Limited, Victoria, Australia

[21] Appl. No.: 133,057

[22] PCT Filed: Apr. 9, 1992

[86] PCT No.: PCT/AU92/00157

§ 371 Date: Nov. 22, 1993

§ 102(e) Date: Nov. 22, 1993

[87] PCT Pub. No.: WO92/18009

PCT Pub. Date: Oct. 29, 1992

[30] Foreign Application Priority Data

Apr. 11, 1991 [AU] Australia ............... PK5558/91

[51] Int. Cl.⁶ .................. A01C 1/00; A01N 63/04
[52] U.S. Cl. .................. 47/58; 435/255.1; 424/93.3; 424/93.51; 426/656; 504/117
[58] Field of Search .................. 800/200; 504/100, 504/116, 117; 426/656, 321, 323, 532; 424/93 R, 93 C, 939, 935, 93.3, 93.51; 47/58; 435/243, 254.1, 255.1, 255.4

[56] References Cited

U.S. PATENT DOCUMENTS 5,041,384  8/1991  Wilson et al. ................ 435/255

FOREIGN PATENT DOCUMENTS

| WO89/07891 | 9/1989 | European Pat. Off. . |
|---|---|---|
| WO/9101641 | 2/1991 | European Pat. Off. . |
| 62-135469 | 6/1987 | Japan . |
| 62-164679 | 7/1987 | Japan . |

OTHER PUBLICATIONS

Janisiewicz (1986) "Biocontrol of Two Postharvest Diseases of Apples with a Yeast" (Abstr.) *Phytopathology*, 76:1133.

Janisiewicz (1987) "Postharvest Biological Control of Blue Mold on Apples" *Postharvest Pathology and Mycotoxins*, 77:481–485.

Janisiewicz (1988) "Biocontrol of Postharvest Diseases of Apples with Antagonist Mixtures" *Phytopathology*, 78:194–198.

Chalutz et al. (1990) "Postharvest Biocontrol of Green and Blue Mold and Sour Rot of Citrus Fruit by *Debaryomyces hansenii*", *Plant Disease*, 74:134–137.

Pusey et al. (1984) "Postharvest Biological Control of Stone Fruit Brown Rot by *Bacillus subtillis*", *Plant Disease*, 68:753–756.

Tronsmo et al. (1980) "Biological Control of *Rotrytis cinerea* on Apple" *Plant Disease*, 64:1009.

Wilson et al. (1985) "Potential for Biological Control of Postharvest Plant Diseases", *Plant Disease*, 69:375–377.

Schaffer et al. (1988) "Development of the protective layer in Golden Delicious apples, 'Loring' peach and willow", *Am. J. Bot.* (Abstr.) 75:45–46.

745,796 Aug. 16, 1991 Wilson et al. Not an issued U.S. Patent document U.S. Agric. Res. Service.

Primary Examiner—Douglas W. Robinson
Assistant Examiner—Elizabeth F. McElwain
Attorney, Agent, or Firm—Scully, Scott, Murphy & Presser

[57] ABSTRACT

Compositions for the treatment/prevention of microbial diseases of fruit comprising an effective amount of at least one yeast strain selected from the species *Rhodotorula glutinis* (Fres.) Harrison and *Rhodotorula mucilaginosa* (Jorg.) Harrison; optionally in association with one or more agriculturally acceptable carriers or excipients are described, as well as methods involving the same. Compositions may be applied to fruit either pre-harvest or post-harvest with post-harvest treatment being preferred. Microbial diseases of fruit which may be treated include blue mold, grey mold, mucor rot and transit rot of fruit.

38 Claims, 1 Drawing Sheet

YEASTS AS A BIOCONTROL FOR MICROBIAL DISEASES OF FRUIT

BACKGROUND OF THE INVENTION

This invention relates to compositions and methods for the treatment/prevention of microbial diseases of fruit utilising specific yeast species strains. The invention also relates to biologically pure cultures of certain yeast strains and combinations thereof which are capable of treating/preventing microbial diseases of fruit.

Worldwide, post-harvest losses of fruits and vegetables have been estimated to be up to 50 percent of harvested crop and much of this is due to microbial diseases such as rots. In the USA, where more attention has been directed towards the post-harvest problem, losses of fruits and vegetables due to post-harvest spoilage still amount to about 24%. Pre-harvest losses of fruits and vegetables are also significant.

Fungicides, which are the principal means of controlling post-harvest rots and other microbial diseases, have recently come under security by health authorities in may countries in view of the potential effect of residues on consumers. According to a US National Science Academy Report (1987), as a class, fungicides account for 60% of the oncogenic risk among all the pesticides used for food produce. Furthermore, the US Environmental Protection Authority has recently proposed a ban on the use of ethylene bis-dithiocarbamates (EBDCs) on food crops. About one-third of all fruit and vegetables in the USA are treated with EBDCs. Benomyl, a fungicide widely used to protect apples and pears from attack by blue and grey mould, was also discontinued for post-harvest use in 1989.

Contamination of the environment by fungicides and risks to the health of farmers are other causes for concern.

A number of organisms are associated with microbial diseases of fruit.

At least 11 species of Penicillium have been isolated from pome fruits naturally infected with blue mould but *P. expansum* is by far the most common and economically important species. Blue mould, also known as soft rot and wet rot, is the most important post-harvest disease of apples and is also important on pears.

Grey mould is the most important post-harvest disease of pears and is second to blue mould in importance on apples. It is caused by the fungus *Botrytis cinerea* Pers. Also known as cluster rot or nest rot, grey mould can cause large losses because of its ability to spread from infected to adjacent healthy fruit during storage. The disease develops more rapidly at cold storage temperature than any other post-harvest decay except Mucor rot.

Mucor rot is caused primarily by *Mucor piriformis* E. Fischer. Mucor rot occurs less consistently than blue mould and grey mould, although in special situations it can cause several losses of apples and pears.

All of these rots are worldwide in occurrence, and affect many types of fruit.

SUMMARY OF THE INVENTION

The traditional method of control of these rots and other microbial diseases is to treat fruit after harvest and before storage with fungicides as discussed above. Benzimidazole and dicarboximide fungicides applied as post-harvest dips, drenches or line sprays are effective against both blue and grey mould. However, fungicide-tolerant strains which are present in most packing-houses, reduce their effectiveness and additional fungicides, e.g., imazalil, have to be used in combination to improve control. This, together with the need for reduced chemical usage on food crops has created a need to develop other methods of controlling post-harvest diseases.

In 1987, Janisiewicz demonstrated that blue mould on apples can be controlled with an antagonistic bacterium and a yeast and in 1988 also reported that two antagonistic microorganisms, viz *Acremonium breve* and a Pseudomonas sp., when tested as mixtures on wounded apples inhibited the development of lesions caused by *P. expansum* and *B. cinerea* (Janisiewicz 1987; Janisiewicz 1988). In 1988, Wisniewski et al. demonstrated the effectiveness of yeast, *Debaryomyces hansenii* to control post-harvest decay of apples caused by *B. cinerea* and, in 1990 Chalutz and Wilson reported that *D. hansenii* was able to inhibit the incidence of green and blue mould and sour rot of several citrus fruit cultivars. Investigations with isolates of *D. Hansenii* have indicated that this antagonist is not particularly effective in controlling blue and green mould of pome and other fruit. The fungus *A. breve* previously proposed for the treatment of microbial disease in fruit is a slow growing fungus which is difficult to produce in large quantities for commercial application.

It is very unpredictable whether particular yeast species would be effective in the treatment/prevention of microbial disease in fruit. Where a yeast strain such as *D. hansenii* is at least partially effective in protecting fruit from microbial diseases, other yeast strains from species capable of growing on fruit may be totally ineffective in treating/preventing microbial disease.

As a result of painstaking investigations by the applicants, it has surprisingly been found that yeast strains selected from the species *Rhodotorula glutinis* (Fres.) Harrison and, *Rhodotorula mucilaginosa* (Jorg.) Harrison, and combinations of one or more such strains are effective in the treatment/prevention of microbial diseases of fruit.

In accordance with the first aspect of this invention there is provided a composition for the treatment/prevention of microbial diseases of fruit comprising an effective amount of at least one yeast strain selected from the species *Rhodotorula glutinis* (Fres.) Harrison and, *Rhodotorula mucilaginosa* (Jorg.) Harrison, optionally in association with one or more agriculturally acceptable carriers or excipients.

Yeast strains of the above species are effective in the treatment/prevention of microbial disease of fruit. Particularly preferred strains are *Rhodotorula glutinis* (Fres.) Harrison strain H10 deposited with the Australian Government Anaytical Laboratory under Accession No. 92/15655; and *Rhodotorula mucilaginosa* (Jorg.) Harrison strain D9 deposited with the Australian Government Analytical Laboratory under Accession No. 92/15656. and derivatives/mutants of said strain effective in the treatment/prevention of microbial disease of fruit.

While this invention is specifically described hereafter with reference to Strains H10 and D9, it is to be understood that the invention is not so limited and extends to any yeast strain of the species *Rhodotorula glutinis* (Fres.) Harrison, and *Rhodotorula mucilaginosa* (Jorg.) Harrison; or mutants/derivatives thereof, optionally in association with one or more agriculturally acceptable carriers or excipients which have activity in the treatment/prevention of microbial diseases of fruits. As described hereinafter, we have devised rapid and routine assays where yeast strains can be screened for the treatment/prevention of microbial diseases of fruit.

For example, fruit such as apples or pears can be wounded and infected with a microorganism which gives rise to a microbial disease (such as, grey mould, blue mould, transit rot, mucor rot or the like). The fruit may then be treated with a composition of a yeast strain and after a few days incubation at 20° to 30° C. it can be visually scanned to see whether or not the onset of microbial disease has been prevented by a candidate yeast strain.

Yeast strains may be readily isolated and cultivated according to standard procedures (for example as described by Phaff, Miller and Mark, *The Life of Yeasts,* 2nd Edition, Harvard University Press 1978; and Devenport, R. R., *Outline Guide to Media and Methods for Studying Yeasts and Yeast Like Organisms, in Biology and Activity of Yeasts,* A. P. London, 1980, both of which are incorporated herein by reference), such as growth on nutrient agar (for example, potato dextrose agar). Yeast strains can be readily typed according to standard procedures (such as described in *Yeasts: Characteristics and Identification* by Barnet et al. [1983] Cambridge University Press) to ascertain whether they belong to the species *Rhodotorula glutinis* (Fres.) Harrison, *Rhodotorula mucilaginosa* (Jorg.) Harrison, *Candida parapsilosis* (Ashf.) Langeron and Talice, and *Candida guilliermondii* (Cast.) Langeron.

This invention extends to derivatives/mutants of the strains H10, and D9 which may be prepared according to standard microbiological methods, such as chemical mutation with mutagenic agents (such as nitrosoguanidine, ethanemethylsulphonate and the like), radiation with an energy source (such as UV radiation, infrared radiation, irradiation with $\alpha$, $\beta$, or $\gamma$ particles from a radiation source, and the like), screening for spontaneous mutants, recombinant DNA techniques and other methodologies as are well known in the art. Derivatives/mutants which are derived from the strains H10, and D9 may differ from the parent strains in respect of one or more of morphology, biochemical characteristics, growth characteristics and the like. Derivatives/mutants which are effective in the treatment/prevention of microbial diseases of fruit are embraced by the present invention. As used herein the terms "derivatives" and "mutants" are synonymous and refer to any strain derived by whatsoever means from the strains H10, D9 and D20.

Compositions may be provided in any of the standard forms known in the art, such as an aqueous suspension, slurry, paste, concentrate or lyophilised form. Lyophilised cultures may be readily re-suspended in aqueous solutions for application to fruit.

Compositions of yeast strains may be in association with one or more agriculturally acceptable carriers or excipients. The term "carriers" includes water, buffer solutions, carbohydrate containing solutions, saline solutions and any other material suitable for the maintenance of yeast strains and the like as are well known in the art. The term "excipient" refers to conventional additives, such as surfactants, antioxidants, nutrients, fungicides and the like as are well known in the art.

Compositions of this invention may additionally comprise a source of calcium, such as calcium chloride or other non-toxic calcium source (for example and proprietary calcium sources such as Stopit (Phosyn International). It has surprisingly been found that compositions containing an effective amount of at least one yeast strain selected from the species *Rhodotorula glutinis* (Fres.) Harrison, *Rhodotorula mucilaginosa* (Jorg.) Harrison; in association with a source of calcium show synergistic/potentiated effects in the treatment/control of microbial diseases. The potentiating effect that calcium has one the yeast strains of this invention is not well understood. Calcium may be provided in an amount from 0.1 to 50% (v/v).

Compositions may additionally comprise anti-scald agents, such as diphenylamine or ethoxyquin and other compounds commonly used in the art for the treatment of fruit.

Additionally, compositions of this invention may include a fungicide, such as imazalil. Given the microbial inhibiting effects of the yeast species of this invention less fungicide than conventionally used would be required.

Compositions of this invention have particular application to the post-harvest treatment of fruit. Harvested fruit is readily amenable to treatment with the compositions of this invention according to standard procedures for the application of compositions, such as pesticides or fungicides, to fruit. Notwithstanding this, the compositions of this invention may be applied to fruit pre-harvest again according to standard procedures.

Preferred fruits which may be treated in accordance with this invention include pome fruits (such as apples and pears), stone fruits (such as peaches, nectarines, apricots, plums, cherries), citrus fruits (such as lemons, oranges, mandarines and limes) and grapes.

Microbial diseases of fruit which may be treated in accordance with this invention include blue mould, grey mould and Mucor rot of fruit as well as other microbial diseases which affect fruit. For reasons which are not well understood, yeast strains selected from the species *Rhodotorula glutinis* (Fres.) Harrison and, *Rhodotorula mucilaginosa* (Jorg.) Harrison are effective in the treatment/prevention of a wide range of microbial diseases of fruit.

The compositions of this invention are generally provided in an amount effective to treat/prevent microbial disease of fruit. This amount will vary depending upon the activity of the yeast strain, the type of fruit being treated, age of the fruit, and like factors. Generally, but without limiting this invention, compositions of this invention may comprise from $1 \times 4^{10}$ cells/ml to $1 \times 10^{12}$ cells/ml. Preferably, compositions comprise in excess of $1 \times 10^7$ cells/ml. The actual amounts of one or more yeast strains is not important as long as the amount is sufficient to treat/prevent microbial disease.

In accordance with a further aspect of this invention there is provided a biologically pure culture of *Rhodotorula glutinis* (Fres.) Harrison strain H10 deposited with the Australian Government Analytical Laboratory under Accession No.

In another aspect of the invention there is provided a biologically pure culture of *Rhodotorula mucilaginosa* (Jorg.) Harrison strain D9 deposited with the Australian Government Analytical Laboratory under Accession No.

In another aspect of this invention there is provided a culture comprising a mixture of at least two of the strains H10 and D9.

The biologically pure cultures may be provided in any form as is well known in the art, such as an aqueous suspension, concentrate, paste, slurry or lyophilised form.

In a further aspect of this invention there is provided a method for the treatment/prevention of microbial disease of fruit comprising applying to said fruit an effective amount of a composition comprising at least one yeast strain selected from the species *Rhodotorula glutinis* (Fres.) Harrison and, *Rhodotorula mucilaginosa* (Jorg.) Harrison, optionally in association with one or more agriculturally acceptable carriers or excipients.

The compositions for use in the method of this invention are as previously described herein.

Preferred yeast strains are selected from *Rhodotorula glutinis* (Fres.) Harrison strain H10 deposited with the Australian Government Anaytical Laboratory under Accession No. 92/15655; and *Rhodotorula mucilaginosa* (Jorg.) Harrison strain D9 deposited with the Australian Government Analytical Laboratory under Accession No. 92/15656; or derivatives/mutants of said strains effective in the treatment/prevention of microbial disease of fruit.

In the method of this invention, compositions of yeast strains may be applied to fruit by methods well known in the art, for example by spraying dipping, drenching or as a mist.

Compositions comprising one or more yeast strains are administered fruit pre-harvest, or post-harvest in an effective microbial inhibiting amount. Generally, but without restricting this invention, such an amount may comprise from $1 \times 10^4$ cells/ml to $1 \times 10^{12}$ cells/ml. Preferably, compositions will comprise at least about $1 \times 10^9$ cells/ml, although this amount may vary according to factors well known in the art. This invention is not limited to a specific concentration of yeast cells, but rather an amount effective to inhibit pathogenic microorganisms which cause disease in fruit.

The method of this invention may be practiced post-harvest, that is, after the fruit has been harvested, and/or may be conducted pre-harvest.

The method of this invention is particularly effective in the treatment blue mould, grey mould, green mould, sour rot and Mucor rot of fruit as well as other microbial diseases of fruit. In particular, this aspect of the invention is effective against the organisms *P. expansum*, *Botrytis cinerea* and *Mucor piriformis*.

Fruit which may be treated in accordance with this invention includes pome fruit (such as apples and pears), stone fruit (such as peaches, nectarines, apricots, plus and cherries), citrus fruit (such as oranges, mandarins, lemons and limes) and grapes as previously described. Apples which may be treated in accordance with this invention include Granny Smith, Red and Golden Delicious, Jonathan, Gala and strains thereof, Fuji, Newton, Macintosh and other well known apple strains. Examples of pears include Packham's Triumph, William's Bon Chretian and Beurre Bosc.

Fruit treated in accordance with the methods of this invention may be stored at standard fruit temperature storage, such as 0° C., 4° C. and room temperature free of the effects of microbial infection or with reduced susceptibility to infection. This is most important as fruit, such as apples and pears, may be stored for a significant time period before sale or use. By way of example, fruit may be stored at temperatures of about 0° or 4° C. up to at least 12 months without spoilage. Fruit treated in accordance with this invention may also be stored in controlled atmosphere (such as 2.5% oxygen and 2.5% carbon dioxide) again without microbial infection, or control of microbial infection.

In a further aspect of this invention there is provided fruit which has been treated with an effective amount of a composition comprising an effective amount of at least one yeast strain selected from the species *Rhodotorula glutinis* (Fres.) Harrison, and *Rhodotorula mucilaginosa* (Jorg.) Harrison. In particular, this aspect of the invention provides fruit which has been treated with a composition comprising *Rhodotorula glutinis* (Fres.) Harrison strain H10 deposited with the Australian Government Anaytical Laboratory under Accession No. 92/15655; and *Rhodotorula mucilaginosa* (Jorg.) Harrison strain D9 deposited with the Australian Government Analytical Laboratory under Accession No. 92/15656; or derivatives/mutants thereof as previously described. Such fruit is resistant to the effects of microbial disease of fruit and thus may be stored for extended time periods and handled without problems of microbial disease infection.

Fruit treated according to this invention includes pome fruit, stone fruit, citrus fruit and grapes. Examples of such fruits include apples, pears, peaches, nectarines, apricots, plums, cherries, grapes, oranges, madarins, lemons and limes.

The novel yeast strains hereafter described have unexpected and very potent activity in the treatment/prevention of microbial disease of fruit.

This invention will now be described with reference to the following non-limiting Figure and Examples.

DESCRIPTION OF THE PREFERRED EMBODIMENTS

EXAMPLE 1

A. Isolation of Yeast Strains

Figure 1:
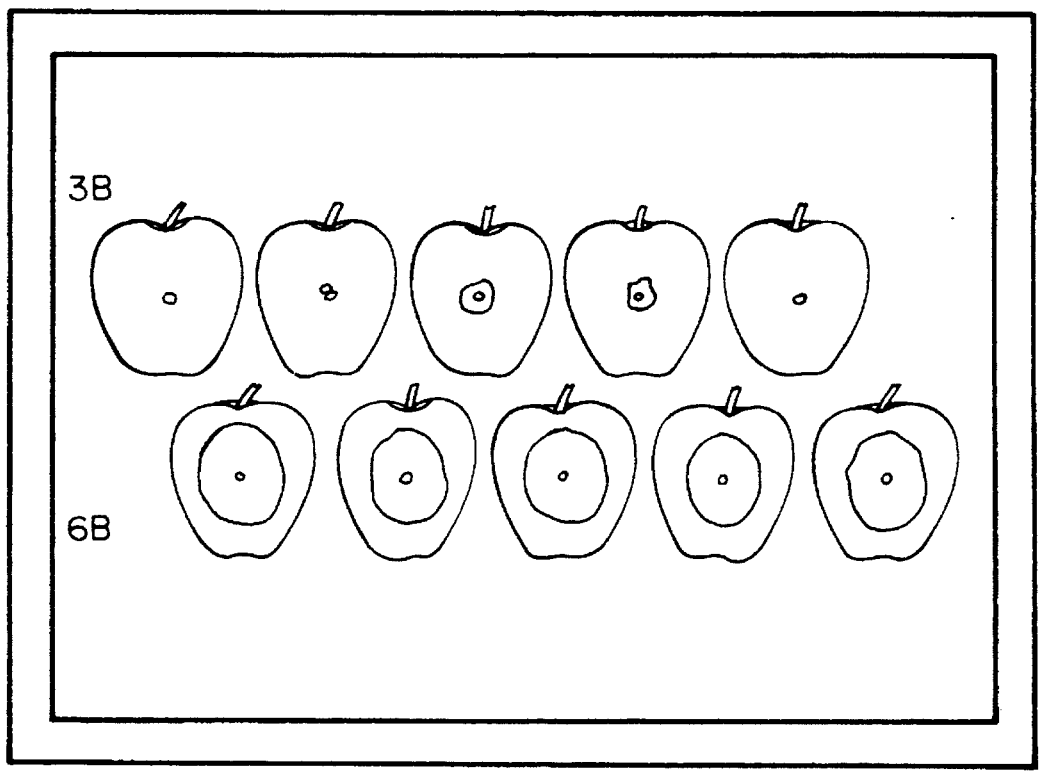
FIG. 1 illustrates the effect of strain D9 on blue mould developments on wounded Golden Delicious apples, photographed 8 days after inoculation with *Penicillium expansum*. Treatment 6B was inoculated with *P. expansum* only.

Yeast strains were isolated according to standard procedures (for example as described by Phaff, Miller and Mrak, *The Life of Yeasts*, 2nd Edition, Harvard University Press, 1978; and Devenport, R. R., *Outline Guide to Media and Methods for Studying Yeasts and Yeast Like Organisms*, in *Biology and Activity of Yeasts*, A. P., London, 1980, both of which are incorporated herein by reference) utilising, for example, various agars containing yeast nutrients and optionally selective agents such as one or more antibiotics.

A large number of yeast strains were isolated from sources such as the surface of fruit, fruit storage crates, butter and other dairy products. Yeast strains were then tested for activity in preventing microbial diseases of fruit according to the routine assay set forth in part C below.

A significant number of the yeast strains isolated (about 50) had no or negligible activity in preventing microbial fruit diseases such as blue mould, grey mould, Mucor rot and transit rot.

Strains from yeast species consistently exhibited activity in treating/preventing microbial diseases of fruit, these species being *Rhodotorula glutinis* (Fres.) Harrison, and *Rhodotorula mucilaginosa* (Jorg.) Harrison. It is currently unclear why these species are active in treating/preventing microbial fruit diseases. The isollation and characterisation of these yeast strains designated H 10, and D9.

Strain H10

Strain H10 was isolated by pressing dichloran-chloramphenicol-rose-bengal agar (King et al. 1979) plates against the inner wall of wooden fruit boxes, used as containers on a commercial orchard. Exposed plates were incubated for 5 days at room temperature and the bacterial and yeast colonies that developed were transferred to potato-dextrose agar (PDA-Oxoid, Unipath Ltd., Basingstoke, Hampshire, England) plates. After cleaning out by re-streaking a few times, clean isolates were transferred to PDA slopes and maintained at 4° C.

Strain D9

This strain was isolated from spoilt butter which was diluted and plated on oxytetracycline-glucose-yeast extract agar and incubated at 25° C. for 5 days. Resulting yeast colonies were isolated and cleaned as described for H10.

Strain D20 (comparative)

The procedure used was identical to D9 but the source was cultured butter milk.

B. Identification of Strains

Yeast species were identified according to standard procedures, such as described in "*Yeasts: Characteristics and Identification*" by Barnett et al. (1983) Cambridge University Press.

The representative yeast strains H10, and D9 were identified by the Centralbureau voor Schimmelcultures, Delft, The Netherlands, as follows:

Strain H10—*Rhodotorula glutinis* (Fres.) Harrison;

Strain D9—*Rhodotorula mucilaginosa* (Jorg.) Harrison and

Comparative Strain D20 is *C. guilliermondii* (Cast.) Langeron and Guerra. (teleomorph *Pichia guilliermondii* Wickerman).

C. Routine Testing Procedures for Effectiveness of Strains Against Microbial Pathogens (i) A standard method for effectiveness was established using apples, although of course, other fruits could be used.

For ease of reference hereafter, yeast strains selected for screening m be referred to as "antagonists" or "antagonistic strains".

In initial screening tests, apple wounds, 3 mm deep and 3 mm in diameter, were inoculated with 30 µl of an aqueous suspension of the antagonistic strain having a concentration $1 \times 10^7$ to $1 \times 10^8$ cells/ml. After hours, the wounds were inoculated with 20 µl of an aqueous suspension of spores of the pathogen, having a concentration of $1 \times 10^4$ to $1 \times 10^5$ spores/ml. Control apples were inoculated with the pathogen only. Inoculated apples were incubated at 24° C. and lesion diameters were measured after 6, 7 or 8 days. Each apple constituted a single replicate and each treatment was replicated 5, 6 or 10 times.

Within a few days an assessment of effectiveness in preventing microbial disease can be made.

(ii) After initial screening as described above, selected antagonists were tested further by dipping fruit in a suspension of the antagonists. Fruit was first dipped in the antagonist suspension and after 2 hours dipped in a suspension of the pathogesn. Alternatively, fruit was dipped in a suspension of the antagonist which was loaded with spores of the pathogen under test. Dipping time was 30 seconds. In such experiments the antagonists were used at a concentration of $1 \times 10^8$ to $1 \times 10^9$ cells/ml and the pathogen at $1 \times 10^4$ spores/ml. Fruit was washed, wiped dry and then wounded in 10 places by puncturing with a nail passed through a rubber stopper. The wounds were conical in shape with a diameter of 2 mm and 4 mm deep. Treated and control fruit were incubated at 24° C. and the percentage of wounds that developed into lesions was recorded after 6, 7 or 8 days.

Both of the above tests are highly artificial, representing a very high pathogen concentration as well as level of wounding D. Storage of Cultures Strains were stored as freeze dried cultures in the dark at room temperature. For routine work, cultures are stored on PDA slopes at 4° C. and replaced every 3–4 months with freeze dried cultures. No loss of activity has been observed with cultures stored in this way. Viable cultures of the strains H10, D9 and D20 have been deposited in the Institute of Plant Sciences Collection at Burnley as well as with the Australian Government Analytical Laboratory as described herein.

E. Cultivation of Strains

For test on antagonistic activity, the strains are normally grown on PDA at 24° C. and 3 to 6 day old cultures were washed off the plates and suspended in sterile distilled water.

When large quantities are required, the strains are cultured in various liquid media but the preferred medium is nutrient broth supplemented with yeast extract and dextrose (NYDB—Nutrient Broth 0.8%, Yeast Extract 0.5%; Dextrose 1.0%). The pH of this medium was 6.6. Liquid cultures were grown in conventional flasks on an orbital shaker (60 rpm) at room temperature for 48 hours, after which the medium was centrifuged (8000 g, 30 min) and the pellet washed with sterile distilled water and resuspended in the same medium. Final concentrations were adjusted by direct cell count using a haemocytometer.

EXAMPLE 2

Effectiveness of strain D9 against blue mould (*P. expansum*) and grey mould (*B. cinerea*)

In the experiment, strain D9 was tested (according to Example 1(c)(i)) together with four other strains (E.a—*Enterobacter aerogenes*, C.a—*Cryptococcus albidus* a standard yeast strain; TV3—*Trichoderma viridie*, a common fungus; B.s—*Bacillus subtilis*, a common bacterium) for its effectiveness against blue and grey mould. There were 5 replicates per treatment and lesions were recorded after 8 days. Results are shown in Table 1 below. Control apples were only inoculated with pathogen.

TABLE 1

Effectiveness of 6 Antagonistic Strains Against Blue Mould (*P. expansum*) and Grey Mould (*B. cinerea*) of Apple

| Antagonist | Mean diameter (mm) of lesion 8 days after inoculation | |
|---|---|---|
| | *P. expansum* | *B. cinerea* |
| E.a | 27.2 | 4.8 |
| C.a. | 17.8 | 5.9 |
| D9 | 6.1 | 4.2 |
| TV3 | 33.2 | 0 |
| B.s | 38.5 | 30.3 |
| Control | 40.9 | 32.1 |

Table 1 clearly shows that the strain D9 is effective in the control of both blue and grey mould. In contrast, none of the other strains tested was considered to be effective against blue mould, while some effectiveness was exhibited against grey mould.

FIG. 1 shows the effectiveness of the strain D9 (designated row 3b) when compared with control apples inoculated only with the pathogen *P. expansum*.

EXAMPLE 3

Effectiveness of Strains H10, D9 and D20 (comparative) Against Grey Mould (*B. cinerea*) of Apple Eleven antagonists were tested in this experiment including the selected test strains H10, D9 and D20. Comparative strains were selected randomly. These strains were: isolated from the surface of peach (A6a); *Trichoderma verdi* (TV3); *Debaryomyces hansenii* a yeast strain previously described to be effective for the treatment of fungal disease of fruit (Hu9); a random yeast isolated from the surface of apricots (Ap2); a yeast isolated from a fruit crate (H9); and a yeast isolated from an apricot surface (A4). Control fruit was inoculated only with pathogen. There were 6 replicates per treatment and lesion diameters were measured 7 days after inoculation. Results (Table 3) demonstrated the effectiveness of the three strains H10, D9 and D20, against grey mould. Some of the other strains investigated were also effective. Strain H9 was found to belong to the yeast species *Geotrichum klebahnii*. This strain is on deposit with the Institute of Plant Sciences Collection at Burnley, Victoria, Australia.

TABLE 2

Effectiveness of 11 Antagonistic Strains Against Grey Mould (*B. cinerea*) of Apple

| Antagonist | Mean lesion diameter (mm) 7 days after inoculation |
|---|---|
| D9 | 2.5 |
| C.a. | 1.3 |
| H10 | 0 |
| A6a | 0 |
| TV3 | 6.7 |
| Hu9 | 8.7 |
| H9 | 0 |
| Ap2 | 5.3 |
| D20 | 0 |
| A9 | 0 |
| A4 | 0 |
| Control | 30.1 |

EXAMPLE 4

Effect of Varying Concentrations of Antagonists and Pathogen on Lesion Development To determine the minimum concentration of antagonist that will completely inhibit lesion development at a given concentration of the pathogen, a number of experiments were carried out using varying concentrations of the antagonists ($2 \times 10^6$–$1.2 \times 10^9$ cells/ml) and pathogens ($0.7 \times 10^3$–$1.2 \times 10^6$ spores/ml). Fruit was wounded and inoculated with the antagonist first and then with the pathogen and lesion diameters were recorded after incubation at 24° C. for 7 days.

Results of one experiment are shown in Table 3. It is evident that about $1 \times 10^9$ cells/ml of the antagonist are required to inhibit lesion development at a pathogen concentration of $1 \times 10^4$ spores/ml under the highly artificial test conditions. Under conventional conditions of apple storage our results indicate that yeast cells in excess of about $1 \times 10^7$ should be effective.

TABLE 3

Effect of Varying Concentrations of Strain D9 on Grey Mould (*B. cinerea*) Development in Apple. Mean Lesion Diameter (mm).

| Concentration of D9 | Concentration of *B. cinerea* (spores/ml) | | | |
|---|---|---|---|---|
| (Cells/ml) | $1.21 \times 10^6$ | $1.21 \times 10^5$ | $1.21 \times 10^4$ | $1.21 \times 10^3$ |
| $1.17 \times 10^9$ | 29.0 | 13.5 | 0 | 0 |
| $0.6 \times 10^9$ | 35.6 | 20.5 | 0 | 0 |
| $0.30 \times 10^9$ | 36.1 | 24.5 | 0 | 0 |
| $0.15 \times 10^9$ | 42.1 | 21.8 | 8.3 | 0 |
| $0.17 \times 10^8$ | 36.4 | 23.3 | 12.9 | 0 |
| SDW-check | 44.6 | 37.4 | 25.1 | 7.9 |

EXAMPLE 5

Effectiveness of Strains H10 and D9 Against Grey Mould (*B. cinerea*) of Apple

In this experiment, strains H10 and D9 were tested for activity against grey mould together with two other yeast (H9 and C.a.). Fruit (cv. Granny Smith) was first dipped in a suspension of the antagonist and 2 hours later dipped in a suspension of the pathogen (according to Example 1 (C)(ii)). Control fruit was dipped only in the pathogen suspension. There were 12 fruit per treatment. Results were observed after 9 days after inoculation and none of the fruit treated with the antagonists developed any lesions, whereas the 12 control fruit had 21 lesions.

EXAMPLE 6

Effectiveness of Strain H10 Against Blue Mould of Apple

Strain H10 and two other strains (C.a. and H9) were tested in this trial on Granny Smith Apples according to the method of Example 1 (C)(ii). There were 12 fruit per treatment and lesions were recorded 7 days after treatment. Again, none of fruit treated with the antagonists developed lesions but the 12 control fruit had 54 lesions (45% infection).

EXAMPLE 7

Effectiveness of H10, D9 and D20 (comparative) Against Mucor Rot of Apple

This test was performed on Granny Smith apples using 10 fruit per treatment. The strains H10, D9 and D20 were compared with strains C.a. and H9 as previously described, and then random isolates D27. A standard chemical treatment which contained iprodione, benomyl and imazalil (0.068%) was included for comparison. Lesions were recorded after incubating fruit for 7 days at 24° C.

Results indicated that strain D20 was as good as the chemical treatment, while H10 and D9 give significant control (Table 6). Strains H9, D27 and C.a. also showed some degree of effectiveness.

TABLE 4

Effectiveness of Strains H10, D9 and D20 and Two Other Strains Against Mucor Rot of Apple

| Treatment | Percentage Infection |
|---|---|
| H9 | 10 |
| H10 | 12 |
| D9 | 12 |
| D20 | 2 |
| D27 | 14 |
| C.a | 14 |
| Chemical | 4 |
| Control | 43 |

In the experiments described so far, fruit was dipped one at a time in 200–300 ml of the antagonist and/or pathogen suspension. The two examples given below describe experiments in which losts of 10 fruit were dipped simultaneously in 2 liters of the appropriate suspension.

The effect of adding calcium to the antagonistic suspension on rot control was also investigated, since calcium has been described as playing an important role in fruit softening and other aspects of fruit quality (Pooviah et al. 1990).

EXAMPLE 8

Effect of Strains H10, With and Without Added Calcium Chloride, on Blue Mould Development in Apples and Pears In this experiment, fruit were wounded and then dipped in a suspension of the antagonist ($1\times10^9$ cells/ml), with and without calcium chloride (2%), and containing $1\times10^4$ spores/ml of *P. expansum*. Control treatments consisted of a solution of calcium chloride and distilled water both having the same concentration of the pathogen. Fruit was incubated at 24° C. and percentage of wounds developing into lesions were recorded after 6 days.

Results (Table 5) indicated that addition of 2% calcium chloride to the antagonistic suspension unexpectedly improved the effectiveness of the antagonist in controlling blue mould in both apples and pears. This effect is synergistic being greater than the sum of H10 protection and calcium protection. In the case of pears, it also appeared that treatment with calcium chloride alone gives significant control of blue mould. It is also evident that fruit can be dipped in bulk in the antagonist suspension and still obtain good control of infection.

TABLE 5

Effectiveness of Strain H10, With and Without Added Calcium Chloride, Against Blue Mould of Apple and Pear

| Treatment | Percentage Infection | |
|---|---|---|
| | Apples | Pears |
| H10 only | 13 | 10 |
| H10 + calcium chloride | 7 | 5 |
| Calcium chloride only | 94 | 27 |
| Control | 98 | 61 |
| LSD (p = 0.05) | 9 | 23 |

EXAMPLE 9

Effect of Strain H10, With and Without Calcium Chloride, on Grey Mould Development in Apples and Pears The procedures used were identical to those in the previous example.

Results (Table 6) show that the addition of calcium chloride to the antagonist suspension improves the control of grey mould. Furthermore, calcium chloride alone has a significant effect on grey mould development but only in pears.

TABLE 6

Effect of Calcium Chloride on the Activity of Strain H10 Against Grey Mould of Apple and Pear

| Treatment | Percentage Infection | |
|---|---|---|
| | Apples | Pears |
| H10 only | 52 | 33 |
| H10 + calcium chloride | 20 | 20 |
| Calcium chloride only | 95 | 52 |
| Control | 100 | 82 |
| LSD (p = 0.05) | 17 | 29 |

EXAMPLE 10

Effect of DPA on the Antagonistic Activity of the Selected Strains

DPA, diphenyl amine, is used as an antiscald agent on some varieties of apples and pears which tend to brown after long cold storage. The object of this experiment was to determine the effect of DPA on the antagonistic activity of the strains H10, D9 and D20 when used in combination. Results are given below.

TABLE 7

Effect of DPA on the Activity 3 Antagonists Against Blue Mould of Apples

| Treatment | Percentage Infection after 7 days |
|---|---|
| H10 | 4 |
| H10 + DPA | 3 |
| D9 only | 2 |
| D9 + DPA | 3 |
| C.a only | 2 |
| C.a. + DPA | 3 |
| DPA only | 26 |
| Control | 38 |

Results show that DPA is compatible with the antagonists tested. In-vitro tests also show that DPA at 2,000 ppm (the highest recommended rate) has no effect on the growth of the antagonists.

EXAMPLE 11

Effectiveness of Strains D9, H10 and D27 Against Blue Mould of Pear Compared with Fungicide Treatment The three antagonists were tested at a concentration of $1\times10^9$ cells/ml. The pathogen concentration was $1\times10^4$ spores/ml.

DPA was added to the appropriate suspension to a final concentration of 1500 ppm. The chemical treatment consisted of iprodione, benomyl and DPA. There were 10 fruit per treatment and 10 wounds per fruit. Treated and control fruit were incubated for 7 days at 24° C. before lesions were recorded.

Results are shown in Table 8.

TABLE 8

Effectiveness of 3 Antagonists Against Blue Mould of Pear, Compared with Fungicide Treatment

| Treatment | Percentage Infection |
| --- | --- |
| D9 only | 17 |
| D9 + DPA | 15 |
| H10 only | 7 |
| H10 + DPA | 11 |
| D27 only | 34 |
| D27 + DPA | 26 |
| Fungicide | 30 |
| Control | 74 |
| LSD (p = 0.05) | 21 |

EXAMPLE 12

Effectiveness of Strains H10, D9 and D20 (comparative) Against Mucor Rot of Apple The concentrations of the antagonists and the pathogen used were the same as in the previous example. In this test, the effect of adding 2% calcium chloride to the antagonistic suspension on the control of blue mould was also investigated. The chemical treatment consisted of iprodione, benomyl and imazalil at the same concentrations as previously indicated. Fruit was incubated at 24° C. and results were recorded 8 days after treatments were applied as set forth in Table 9.

TABLE 9

Effectiveness of Strains H10, D9 and D20, With and Without Calcium Chloride, Against Mucor Rot of Apple, Compared with Fungicide Treatment

| Treatment | Percentage Infection |
| --- | --- |
| H10 only | 7 |
| H10 + calcium chloride | 0 |
| D9 only | 4 |
| D9 + calcium chloride | 0 |
| D20 only | 7 |
| D20 + calcium chloride | 0 |
| Chemical | 2 |
| Control | 79 |

These experiments (Examples 11 and 12) indicate that the three selected strains control post-harvest rots of pome fruit as effectively as the currently used chemical treatment. The strains are also compatible with DPA and the addition of calcium chloride to the antagonistic dip improves control in a synergistic manner.

EXAMPLE 13

A number of investigations were carried out to determine if the selected antagonists would be active after holding treated fruit at 0°–1° C., the usual temperature at which fruit, such as pome fruit, is stored.

A. Effectiveness of 5 strains against blue mould of apple after holding treated fruit at 1° C. for 9 days The antagonists used were strains H],H10, D9, D 20 and C.a. Fruit was wounded and dipped in a suspension of the antagonist loaded with spores of *P. expansum*, held at 1° C. for 9 days and then transferred to 24° C. for 7 days. A fungicide treatment was included for comparison. Results are shown in Table 10.

TABLE 10

Effectiveness of 4 Antagonistic Strains Against Blue Mould of Apple, After Holding Treated Fruit for 9 Days at 1° C.

| Antagonist | Percentage Infection after 1 week at 24° C. |
| --- | --- |
| H9 | 24 |
| H10 | 9 |
| D9 | 6 |
| D20 | 5 |
| Chemical | 2 |
| Control | 54 |

The strains H10, D9 and D20 (comparative) were clearly effective in protecting fruit from blue mould.

B. Effectiveness of 6 antagonists against grey mould of pear after holding treated fruit at 0° C. for 10 days Procedures used were similar to previous examples. Treated and control fruit were held at 0° C. for 10 days and then transferred to 24° C. for 7 days before infection was recorded (Table 11).

TABLE 11

Effectiveness of 6 Antagonists Against Grey Mould of Pear After Holding Treated Fruit at 0° C. for 10 Days

| Antagonist | Percentage infection after 1 week at 24° C. |
| --- | --- |
| H9 | 43 |
| H10 | 4 |
| D9 | 12 |
| D20 (Comparative) | 10 |
| D27 | 31 |
| C.a. | 43 |
| Chemical | 0 |
| Control | 86 |

The two examples quoted indicate that three antagonists, viz. H10, D9 and D20 (comparative), will retain their activity even after the fruit is held in cold storage for up to 10 days. Further experiments indicate that the strains H9, D10 and D20 provide protection against infection for extended periods such as used for the cold storage of fruit.

EXAMPLE 15

The effectiveness of selected antagonists against transit rot was also investigated. Transit rot caused by *Rhizopus stolonifer* on both apples and pears in most countries where pome fruit is grown but is seldom serious. However, when it occurs it can be quite troublesome.

In this experiment D9 and D20 (comparative) were tested with Granny Smith apples. Fruit was wounded and dipped in an aqueous suspension of the 3 antagonists and 2 hours later dipped in a suspension of sporangiospores of *R. stolonifer*. There were 12 fruit per treatment. Control fruit was treated with the pathogen only. Infection was recorded after incubating the fruit at 24° C. for 7 days.

Results (Table 12) showed that all 3 antagonists were highly effective in checking the development of transit rot on apples. Three of the control fruit were almost completely rotten on the 7th day.

TABLE 12

Effectiveness of 2 Antagonists Against Transit Rot
(*Rhizopus stolonifer*) of Apple

| Antagonist | Percentage infection after 7 days |
|---|---|
| D20 | 0 |
| D9 | 0.8 |
| Control | 25 |

The above examples show that strains of the yeast species *Rhodotorula glutinis* (Fres.) Harrison and *Rhodotorula mucilaginosa* (Jorg.) Harrison, are effective in the control of microbial diseases of fruit, in particular, blue and grey mould, Mucor rot of apple and pear and transit rot. It is to be emphasised that the conditions of pathogen infection are very severe and represent a much higher level of pathogen attack than experienced under normal conditions. The level of wounding is also very much greater than the natural incidence.

This invention has been exemplified with reference to strains H10, D9 although it is to be appreciated the invention is not so limited and extends to any strain of the yeast species *Rodotorula glutinis* (Fres.) Harrison and *Rhodotorula mucilaginosa* (Jorg.) Harrison, or combinations thereof. The selected strains H10 and D9 are particularly advantageous due to their effectiveness in controlling microbial fruit diseases, vigorous growth characteristics and lack of any pathological effects.

This invention in its various aspects also extends to yeast strains of the species *Geotrichum klebahnii* as represented by the strain H9 (isolated from a fruit crate) and *E. albidus* (C.a.) which as described herein are effective in the control of microbial disease in fruit. These strains have practical disadvantages (when compared with H10 and D9) associated with growth rate and the like which may be overcome by modification of culture conditions.

The examples have been largely concerned with post-harvest treatment of fruit where the application and compositions comprising at least one yeast strain as described herein can be readily carried out. The invention is clearly also applicable to pre-harvest treatment of fruit where the compositions of this invention would be applied to the fruit when still on the plant.

Yeast strains of the species *Rhodotorula glutinis* (Fres.) Harrison and, *Rhodotorula mucilaginosa* (Jorg.) Harrison, are as effective as fungicides currently used in horticulture to prevent microbial diseases of fruit. Accordingly, the compositions of this invention and methods involving the same provide alternative treatment which do not have the problems of toxicity posed by fungicides.

Surprisingly, organisms of the species *Rhodotorula glutinis* (Fres.) Harrison and, *Rhodotorula mucilaginosa* (Jorg.) Harrison, are not affected by fungicides, belonging to the benzimidazole and dicarboximide groups, which are used in field applications for the control of pre-harvest and post-harvest diseases. Accordingly, compositions described herein may also contain fungicides in reduced amounts thus overcoming problems of toxicity associated with such fungicides.

The yeast strains referred to in the examples have been shown to survive in a range of temperatures in which fruit is stored and still be effective.

The mechanism by which the yeast strains of this invention are effective in the treatment/prevention of microbial disease is currently unclear. They do not appear to produce antibiotics like certain bacteria or fungi. When applied to wounds on fruit they appear to grow until they have used all the nutrients available and in this way may be depriving the fungal spores of nutrients for their development. When applied alone to wounds they do not cause any obvious rot or infection.

DEPOSIT DETAILS

All the strains listed hereunder were deposited with the Australian Government Analytical Laboratories, A Budapest Treaty Depository, of P.O. Box 385, Pymble, 2073, New South Wales, Australia:

| Yeast Strain | Accession No. | Deposit Date |
|---|---|---|
| *Rhodotorula glutinis* H10 | 92/15655 | 6th April, 1992 |
| *Rhodotorula mucilaginosa* D9 | 92/15656 | 6th April, 1992 |
| *guilliermodii* (Cast) Langeron and Guerra (teleomorph *Pichia guilliermodii* Wickerman) | 92/15657 | 6th April, 1992 |

REFERENCES

The references set out hereunder are specifically incorporated into the specification by reference.

Barnett, J. A., Payne, R. W. and Yarrow, D., 1983. *Yeasts: Characteristics and Identification*, Cambridge Univ. Press, Cambridge Chalutz, E. and Wilson, C. 1990. Postharvest biocontrol of green and blue mould and sour rot of citrus fruit by *Debaryomyces Hansenii* Plant Disease 74:134–137

Janisiewicz, W. J. 1987. Post-harvest biological control of blue mould on apples. *Phytopathology* 77:481–485

Janisiewicz, W. J. 1988. Biocontrol of postharvest diseases of apples with antagonist mixtures. *Phytopathology* 78:194–198

King, A. D., Hocking, A. D., and Pitt, J. I. 1979. Dictoran-rose bengal medium for enumeration and isolation of moulds from foods. *Appl. Environ. Microbiol.* 37:959–964

Poovia, B. W., Glenn, G. M. and Reddy, A. S. N. 1990. Calcium and fruit softening: Physiology and biochemistry. *Horticultural Reviews* 10:107–152

Wisniewski, M., Wilson, C., Chalutz, E. and Hershberger, W. 1988. Biological control of postharvest diseases of fruit. Inhibition of Botrytis rot on apple by an antagonistic yeast. *Proc. Electron. Microsc. Soc. Am.* 46:290–291

I claim:

1. A composition for the treatment or prevention of microbial diseases of fruit comprising an effective amount of at least one yeast strain selected from the species *Rhodotorula glutinis* (Fres.) Harrison, and *Rhodotorula mucilaginosa* (Jorg.) Harrison, optionally in association with one or more agriculturally acceptable carriers or excipients.

2. A composition according to claim 1 wherein said at least one yeast strain is selected form *Rhodotorula glutinis* (Fres.) Harrison strain H10 deposited with the Australian Government Analytical Laboratory under Accession No. 92/15655; and *Rhodotorula mucilaginosa* (Jorg.) Harrison strain D9 deposited with the Australian Government Analytical Laboratory under Accession No. 92/15656; or derivatives or mutants of said strains effective in the treatment or prevention of microbial disease of fruit.

3. A method for the treatment or prevention of microbial disease of fruit comprising applying to said fruit an effective amount of a composition comprising at least one yeast strain selected from the species *Rhodotorula glutinis* (Fres.) Harrison and *Rhodotorula mucilaginosa* (Jorg.) Harrison, optionally in association with one or more agriculturally acceptable carriers or excipients.

4. A method according to claim 3 wherein said composition comprises at least one yeast strain selected from *Rhodotorula glutinis* (Fres.) Harrison strain H10 deposited with the Australian Government Analytical Laboratory under Accession No. 92/15656; or derivatives or mutants of said strains effective in the treatment or prevention of microbial disease of fruit.

5. A method for the treatment or prevention of mold or rot of some fruits caused by the organisms *Penicillium expansum, Botyris cinerea* and *Mucor piriformis* comprising applying to said fruit an effective amount of a composition comprising at least one yeast strain selected from the species *Rhodotorula glutinis* (Fres.) Harrison and *Rhodotorula mucilaginosa* (Jorg.) Harrison optionally in association with one or more agriculturally acceptable carriers or excipients.

6. The method of claim 4, wherein *Rhodotorula glutinis* (Fres.) Harrison strain H10 deposited with the Australian Government analytical Laboratory under accession as 92/15655 is applied to pears in the treatment or prevention of grey mold, in a composition comprising at least $1 \times 10^7$ cells/ml.

7. A composition according to claim 1 which additionally comprises a source of calcium.

8. A composition according to claim 7 wherein said source of calcium is calcium chloride.

9. A composition according to claim 1 which additionally comprises an antiscald agent.

10. A composition according to claim 9 wherein said antiscald agent is diphenylamine or ethoxyquin.

11. A composition according to claim 1 in the form of an aqueous suspension of said one or more yeast strains.

12. A composition according to claim 1 comprising at least $1 \times 10^7$ cells/ml.

13. A composition according to claim 1 which is lyophilised.

14. A composition according to claim 1 for the treatment or prevention of microbial pre-harvest or post-harvest disease of fruit.

15. A composition according to claim 14 for the treatment or prevention of blue mould, grey mould, and mucor rot of fruit.

16. A composition according to claim 14 for the treatment or prevention of mould or rot of fruit caused by the organisms *P. expansum, Botrytis cinerea,* and *Mucor piriformis.*

17. A composition according to claim 1 for the treatment or prevention of microbial pre-harvest and post-harvest diseases of pome fruit.

18. A composition according to claim 17 wherein said pome fruit is selected from apples and pears.

19. A composition according to claim 1 for the treatment or prevention of microbial pre-harvest and post-harvest disease of stone fruit.

20. A composition according to claim 19 wherein said stone fruit is selected from peaches, nectarines, apricots, plums and cherries.

21. A composition according to claim 1 for the treatment or prevention of microbial pre-harvest and post-harvest diseases of grapes.

22. A composition according to claim 1 for the treatment or prevention of microbial pre-harvest and post-harvest diseases of citrus fruits.

23. A composition according to claim 22 wherein said citrus fruit is selected from oranges, mandarins, lemons and limes.

24. A method according to claim 3 wherein said composition is an aqueous suspension of said one or more yeast strains.

25. A method according to claim 3 wherein said composition is a composition according to claim 1.

26. A method according to claim 3 wherein said composition is applied to fruit by spraying, dipping, drenching or as a mist.

27. A method according to claim 3 wherein said composition comprises at least $1 \times 10^7$ cells/ml.

28. A method according to claim 3 wherein said composition is applied to said fruit post-harvest.

29. A method according to claim 3 wherein said composition is applied to fruit pre-harvest.

30. A method according to claim 3 for the treatment or prevention of microbial pre-harvest and post-harvest diseases of pome fruit.

31. A method according to claim 30 wherein said pome fruit is selected from apples and pears.

32. A method according to claim 3 for the treatment or prevention of microbial pre-harvest and post-harvest diseases of stone-fruit.

33. A method according to claim 32 wherein said stone fruit is selected from peaches, nectarines, apricots, plums and cherries.

34. A method according to claim 3 for the treatment or prevention of microbial pre-harvest and post-harvest diseases of grapes.

35. A method according to claim 3 for the treatment or prevention of microbial pre-harvest and post-harvest diseases of citrus fruits.

36. A method according to claim 35 wherein said citrus fruit is selected from oranges, mandarins, lemons and limes.

37. A method according to claim 3 for the treatment of blue mould, grey mould, Mucor rot and transit rot of fruit.

38. A method according to claim 3 which is a method for the treatment of mould or rot of fruit caused by the organisms *P. expansum, Botrytis cinerea* and *Mucor piriformis.*

\* \* \* \* \*